(12) United States Patent
Kehres et al.

(10) Patent No.: US 10,485,556 B2
(45) Date of Patent: Nov. 26, 2019

(54) QUICK-CONNECT ANTI-ROTATION PEG/DRILL BIT COMPONENT

(71) Applicant: Biomet Manufacturing, LLC, Warsaw, IN (US)

(72) Inventors: Clinton E. Kehres, Warsaw, IN (US); Jason M. Hurst, New Albany, OH (US)

(73) Assignee: Biomet Manufacturing, LLC, Warsaw, IN (US)

( * ) Notice: Subject to any disclaimer, the term of this patent is extended or adjusted under 35 U.S.C. 154(b) by 314 days.

(21) Appl. No.: 15/480,001

(22) Filed: Apr. 5, 2017

(65) Prior Publication Data

US 2017/0202561 A1    Jul. 20, 2017

Related U.S. Application Data

(60) Continuation of application No. 15/078,261, filed on Mar. 23, 2016, which is a division of application No. 13/744,737, filed on Jan. 18, 2013, now Pat. No. 9,320,527.

(51) Int. Cl.
| | |
|---|---|
| *A61B 17/16* | (2006.01) |
| *A61B 17/17* | (2006.01) |
| *A61F 2/40* | (2006.01) |
| *A61B 17/00* | (2006.01) |

(52) U.S. Cl.
CPC ........ *A61B 17/1617* (2013.01); *A61B 17/162* (2013.01); *A61B 17/1684* (2013.01); *A61B 17/1778* (2016.11); *A61F 2/4081* (2013.01); *A61B 2017/00477* (2013.01)

(58) Field of Classification Search
CPC .............. A61B 17/1617; A61B 17/162; A61B 17/1684; A61B 17/78; A61B 2017/1778; A61B 2017/00477; A61F 2/4081
See application file for complete search history.

(56) References Cited

U.S. PATENT DOCUMENTS

| | | | | |
|---|---|---|---|---|
| 4,353,670 A | * | 10/1982 | Jorgensen | ........... B23B 31/1075 408/193 |
| 4,381,770 A | * | 5/1983 | Neufeld | ............. A61B 17/1721 606/67 |
| 4,514,117 A | * | 4/1985 | Scott | ................... B23B 31/1075 279/77 |
| 5,231,900 A | * | 8/1993 | Deri | ...................... B25B 23/045 81/434 |

(Continued)

OTHER PUBLICATIONS

"U.S. Appl. No. 13/744,737, Final Office Action dated Apr. 9, 2015", 8 pgs.

(Continued)

*Primary Examiner* — Zade Coley
(74) *Attorney, Agent, or Firm* — Schwegman Lundberg & Woessner, P.A.

(57) ABSTRACT

A quick-connect drill bit assembly comprising a drive shank and a drill bit releasably attached to the drive shank, the drill bit being configured to bore a first hole in a bone through a drill guide. A portion of the drill bit is configured to remain within the first hole after the drive shank is detached therefrom, the drill bit being configured to prevent the drill guide from rotating with respect to the bone as a second hole is bored into the bone.

19 Claims, 8 Drawing Sheets

(56) References Cited

U.S. PATENT DOCUMENTS

| | | | | |
|---|---|---|---|---|
| 5,250,050 A * | 10/1993 | Poggie | A61B 17/154 | 606/79 |
| 5,382,251 A * | 1/1995 | Hood | A61B 17/8847 | 606/2 |
| 5,540,695 A * | 7/1996 | Levy | A61B 17/15 | 606/87 |
| 5,586,847 A * | 12/1996 | Mattern, Jr. | B23B 51/108 | 279/145 |
| 5,634,927 A * | 6/1997 | Houston | A61B 17/1735 | 606/79 |
| 5,891,150 A * | 4/1999 | Chan | A61B 17/1714 | 606/96 |
| 6,332,887 B1 * | 12/2001 | Knox | A61B 17/1728 | 606/105 |
| 6,354,177 B2 * | 3/2002 | Peters | B25B 15/001 | 81/177.4 |
| 6,364,910 B1 * | 4/2002 | Shultz | A61B 17/1659 | 606/86 R |
| 6,780,189 B2 * | 8/2004 | Tidwell | A61B 17/162 | 606/170 |
| 7,753,959 B2 * | 7/2010 | Berelsman | A61F 2/4081 | 623/19.11 |
| 7,896,917 B2 * | 3/2011 | Walters | A61B 17/1764 | 623/13.11 |
| 9,320,527 B2 | 4/2016 | Kehres et al. | | |
| 2002/0095214 A1 * | 7/2002 | Hyde, Jr. | A61B 17/1604 | 623/18.12 |
| 2003/0065332 A1 * | 4/2003 | TenHuisen | A61B 17/8685 | 606/312 |
| 2007/0055380 A1 * | 3/2007 | Berelsman | A61F 2/4081 | 623/19.11 |
| 2008/0153067 A1 * | 6/2008 | Berckmans | A61C 8/0001 | 433/213 |
| 2008/0161815 A1 * | 7/2008 | Schoenefeld | A61B 17/154 | 606/87 |
| 2008/0167653 A1 * | 7/2008 | Watlington | A61B 17/1615 | 606/81 |
| 2011/0301611 A1 * | 12/2011 | Garcia | A61B 17/162 | 606/80 |
| 2012/0239042 A1 * | 9/2012 | Lappin | A61B 17/1684 | 606/80 |
| 2012/0239043 A1 * | 9/2012 | Lappin | A61B 17/1631 | 606/80 |
| 2012/0330316 A1 * | 12/2012 | Berelsman | A61B 17/1604 | 606/87 |
| 2012/0330317 A1 * | 12/2012 | Berelsman | A61F 2/30756 | 606/88 |
| 2013/0204258 A1 * | 8/2013 | Goodfellow | A61B 17/155 | 606/88 |
| 2014/0207141 A1 | 7/2014 | Kehres et al. | | |
| 2016/0199069 A1 | 7/2016 | Kehres et al. | | |
| 2017/0202565 A1 | 7/2017 | Kehres et al. | | |

OTHER PUBLICATIONS

"U.S. Appl. No. 13/744,737, Non Final Office Action dated Sep. 4, 2015", 12 pgs.

"U.S. Appl. No. 13/744,737, Non Final Office Action dated Dec. 12, 2014", 10 pgs.

"U.S. Appl. No. 13/744,737, Notice of Allowance dated Dec. 23, 2015", 8 pgs.

"U.S. Appl. No. 13/744,737, Response filed Mar. 6, 2015 to Non Final Office Action dated Dec. 12, 2014", 9 pgs.

"U.S. Appl. No. 13/744,737, Response filed Aug. 6, 2015 to Final Office Action dated Apr. 9, 2015", 10 pgs.

"U.S. Appl. No. 13/744,737, Response filed Nov. 12, 2014 to Restriction Requirement dated Nov. 6, 2014", 4 pgs.

"U.S. Appl. No. 13/744,737, Response filed Nov. 25, 2015 to Non Final Office Action dated Sep. 4, 2015", 13 pgs.

"U.S. Appl. No. 13/744,737, Restriction Requirement dated Nov. 6, 2014", 6 pgs.

"U.S. Appl. No. 15/078,261, Preliminary Amendment filed Mar. 24, 2016", 5 pgs.

"Comprehensive® Total Shoulder System", Biomet Orthopedics, Surgical Technique Brochure, Form No. BMET0206.0 REV000012, (2012), 56 pgs.

"U.S. Appl. No. 15/078,261, Advisory Action dated Apr. 11, 2019", 3 pgs.

"U.S. Appl. No. 15/078,261, Final Office Action dated Feb. 27, 2019", 11 pgs.

"U.S. Appl. No. 15/078,261, Non Final Office Action dated May 28, 2019", 12 pgs.

"U.S. Appl. No. 15/078,261, Non Final Office Action dated Dec. 27, 2018", 10 pgs.

"U.S. Appl. No. 15/078,261, Response filed Feb. 7, 2019 to Non Final Office Action dated Dec. 27, 2018", 11 pgs.

"U.S. Appl. No. 15/078,261, Response filed Apr. 1, 2019 to Final Office Action dated Feb. 27, 2019", 10 pgs.

"U.S. Appl. No. 15/480,071, Non Final Office Action dated Apr. 12, 2019", 12 pgs.

"U.S. Appl. No. 15/480,071, Preliminary Amendment filed Apr. 6, 2017", 7 pgs.

\* cited by examiner

QUICK-CONNECT ANTI-ROTATION PEG/DRILL BIT COMPONENT

CLAIM OF PRIORITY

This application is a continuation of U.S. patent application Ser. No. 15/078,261, filed on Mar. 23, 2016, which is a divisional of U.S. patent application Ser. No. 13/744,737, filed on Jan. 18, 2013, now issued as U.S. Pat. No. 9,320,527, the benefit of priority of each of which are claimed hereby, and each of which are incorporated by reference herein in its entirety.

TECHNICAL FIELD

The present application generally relates to a surgical drill component, and more particularly to a quick-connect anti-rotation peg/drill bit component that can be used as part of a glenoid technique during a shoulder surgery.

BACKGROUND OF THE INVENTION

The statements in this section merely provide background information related to the present disclosure and should not be construed as constituting prior art.

A natural shoulder joint may undergo degenerative changes due to a variety of etiologies. When these degenerative changes become so far advanced and irreversible, it may ultimately become necessary to replace a natural shoulder joint with a prosthetic shoulder joint. When implantation of a shoulder joint prosthesis becomes necessary, the natural head portion of the humerus can be resected and a cavity created in the intramedullary canal of the host humerus for accepting a humeral component Moreover, the glenoid cavity positioned at the lateral edge of the scapula may also be resurfaced and shaped to accept the glenoid component. The humeral component includes a head portion used to replace the natural head of the humerus, while the glenoid component generally includes an articulating surface which is engaged by the head portion of the humeral component.

It is generally known in the art to provide a total shoulder joint prosthesis having a glenoid component, as discussed above. Current glenoid replacement surgical techniques, however, suffer from some disadvantages, particularly as they require the surgeon to perform numerous bone preparation steps before the glenoid component can be surgically implanted. More particularly, since glenoid components are subject to various types of loading by the head portion of the humeral component, the glenoid component must offer a stable and secure articulating surface. To achieve this, some glenoid components provide peripheral pegs which are inserted and cemented into holes bored into the glenoid cavity. Some of the pegged glenoid components utilize up to five peripheral pegs in order to stabilize and secure the glenoid component to the scapula. Current glenoid replacement procedures require pre-drilled holes to be formed in the bone for each peripheral peg of the glenoid component. To achieve this, typically a guide is placed on the glenoid that provides a path for each peripheral peg hole to be drilled. After each hole is drilled, an anti-rotation peg is inserted into that respective hole of the guide to ensure the next drilled hole is properly aligned. By requiring multiple holes to be separately drilled into the bone and anti-rotation pegs to be individually placed in each drilled hole, not only is the process time-consuming, but it also increases the possibility that a drilling misalignment will occur during the bone preparation process.

What is needed then is a device that can be incorporated into a glenoid replacement surgical technique that minimizes or eliminates some of the above-mentioned disadvantages. The present application is intended to improve upon and resolve some of these known deficiencies of the art.

SUMMARY OF THE INVENTION

In accordance with one aspect of the present application, a quick-connect drill bit assembly is provided and comprises a drive shank and a drill bit releasably attached to the drive shank, the drill bit being configured to bore a first hole in a bone through a drill guide. In accordance with this aspect of the present application, a portion of the drill bit is configured to remain within the first hole after the drive shank is detached therefrom. The drill bit is also configured to prevent the drill guide from rotating with respect to the bone as a second hole is bored into the bone.

According to another aspect of the present application, a quick-connect drill bit assembly comprises a drill bit configured to penetrate bone through an opening of a drill guide and a drive shank having an opening disposed on one end, the opening being configured to receive an attachment post of the drill bit and establish a releasably engageable magnetic connection therebetween. In accordance with this aspect of the application, the drill bit is configured to prevent the drill guide from rotating with respect to the bone after the drill bit is detached from the drive shank and left inserted into the bone through the guide plate.

In accordance with still another aspect of the present application, a method of preventing a drill guide from rotating with respect to a glenoid cavity during a peripheral peg hole drilling procedure is provided. In accordance with this illustrative aspect of the present application, the method comprises the steps of advancing a drill guide over an alignment pin extending from the glenoid cavity; using a drill to create a first hole in the glenoid cavity through a first guide hole of the drill guide by rotatably activating a first drill bit; disassociating the drill from the first drill bit while the first drill bit is still inserted into the glenoid cavity through the guide plate; and using the drill to create a second hole in the glenoid cavity through a second guide hole of the drill guide by rotatably activating a second drill bit, wherein the first drill bit helps prevent the drill guide from rotating with respect to the glenoid cavity as the second hole is created.

Still other objects and benefits of the application will become apparent from the following written description along with the accompanying figures.

BRIEF DESCRIPTION OF THE DRAWINGS

The above-mentioned aspects of the present application and the manner of obtaining them will become more apparent and the teachings of the present application itself will be better understood by reference to the following description of the embodiments of the present application taken in conjunction with the accompanying drawings, wherein:

FIG. 1A represents a side cross-sectional view of the illustrative quick-connect anti-rotation peg/drill bit assembly taken along line 1A-1A of FIG. 1;

Figure 1:
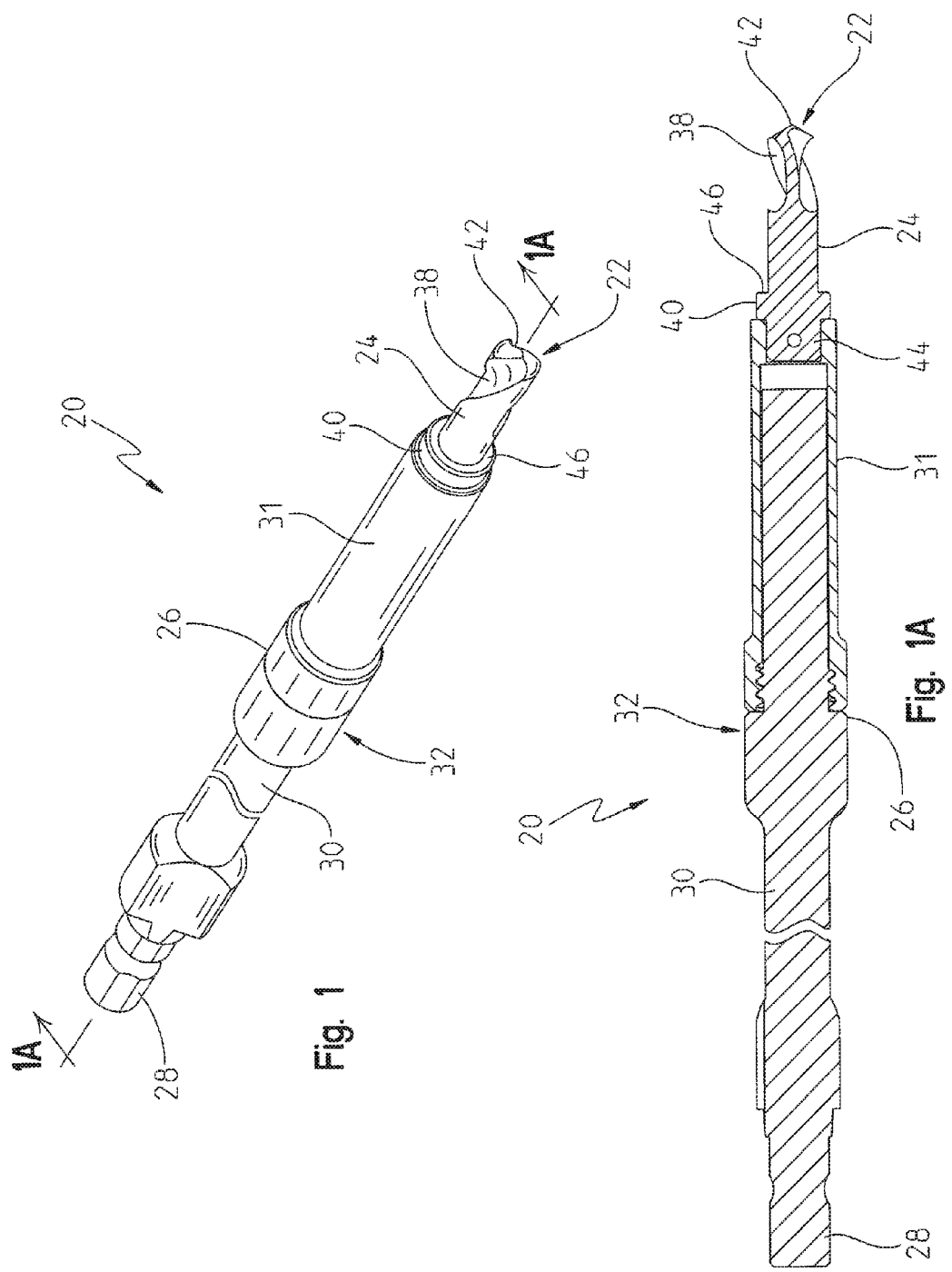
FIG. 1 represents a perspective view of an illustrative quick-connect anti-rotation peg/drill bit assembly in accordance with the teachings of the present application.

Corresponding reference characters indicate corresponding parts throughout the several views. Although the exemplification set out herein illustrates embodiments of the present application, in several forms, the embodiments disclosed below are not intended to be exhaustive or to be construed as limiting the scope of the present application to the precise forms disclosed.

DETAILED DESCRIPTION

The embodiments of the present application described below are not intended to be exhaustive or to limit the teachings of the present application to the precise forms disclosed in the following detailed description. Rather, the embodiments are chosen and described so that others skilled in the art may appreciate and understand the principles and practices of the present application.

Unless defined otherwise, all technical and scientific terms used herein have the same meaning as commonly understood by one of ordinary skill in the art to which this application belongs. Although any method and materials similar or equivalent to those described herein can be used in the practice or testing of the present application, the specific methods and materials are now described. Moreover, the techniques employed or contemplated herein are standard methodologies well known to one of ordinary skill in the art and the materials, methods and examples are illustrative only and not intended to be limiting.

Before discussing in detail the substantive aspects of the present application, it should be generally understood and appreciated herein that various techniques for preparing a glenoid as part of a shoulder procedure, including techniques for appropriately sizing and reaming the glenoid prior to implantation, are readily known within the art and are therefore not discussed in detail within this application. The present application is intended to encompass any available or known glenoid preparation procedure without straying from the contemplated scope of the present application. Therefore, the present application is not intended to be limited herein.

After the glenoid cavity has been prepared, conventional surgical procedures typically require that a plurality of fixed glenoid peg accepting holes be individually drilled into the resected glenoid. To accomplish this, a drilling guide is placed on the glenoid and is used as a template to provide a path for each peripheral peg hole to be drilled. After each hole is drilled, an anti-rotation peg is inserted into that respective hole of the guide to ensure that the drill guide doesn't rotate or move, thereby disrupting the drill guide from being properly aligned and placed prior to the next peripheral peg hole being created.

The present teachings, however, eliminate the need to have separate anti-rotation pegs inserted into the bone after each hole is drilled, and instead provide a means for utilizing the actual drill bits used to create the peripheral peg holes also as anti-rotation pegs. More particularly, when a peripheral peg hole is drilled into the glenoid cavity through the drill guide, the friction from the drill/bone interface allows the drill bit to stay in place. By keeping the drill bit in place through the drill guide, the drill guide is thereby prevented (or at least discouraged) from freely rotating with respect to the glenoid cavity as the subsequent peripheral peg holes are drilled into the glenoid through the drill guide. Additional details regarding this aspect of the present application are now discussed in more detail below.

Referring generally to FIGS. 1 and 1A, a quick-connect anti-rotation peg/drill bit assembly 20 according to the teachings of the present application is shown. The anti-rotation peg/drill bit assembly 20 has a distal working end 22 including a drill bit 24 for drilling peripheral peg holes into a glenoid cavity during a shoulder procedure. The drill bit assembly 20 includes a drive shank 26 which terminates in a drive attachment 28 that is configured to releasably couple with the chuck of a corresponding orthopedic drill that is designed to impart rotating motion to the drill bit 24.

While the drive shank 26 may be made of one integral piece of material, in accordance with certain aspects of the present application, the drive shank 26 can also be made of two or more components. For instance, in accordance with one aspect of the present application, the drive shank 26 includes first and second sections (30 and 31) that are adjoined to form a common collar portion 32. While the first and second sections 30, 31 may be releasably coupled to one another by any known means within the art, in accordance with certain specific aspects of the present teachings, the sections are coupled to one another by a threaded engagement.

Figure 2:
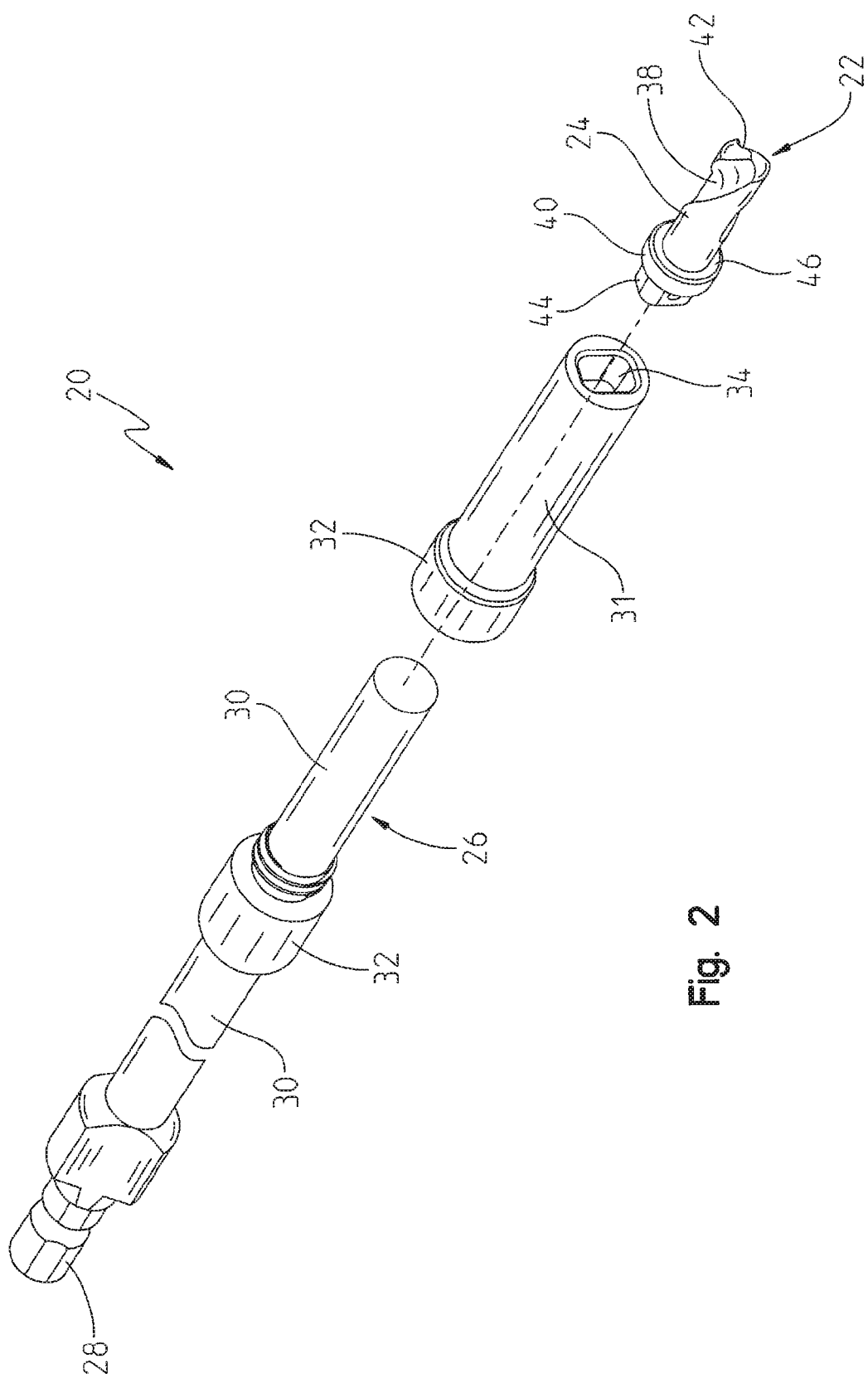
FIG. 2 represents a perspective exploded view of the illustrative quick-connect anti-rotation peg/drill bit assembly of FIG. 1.
Figure 3:
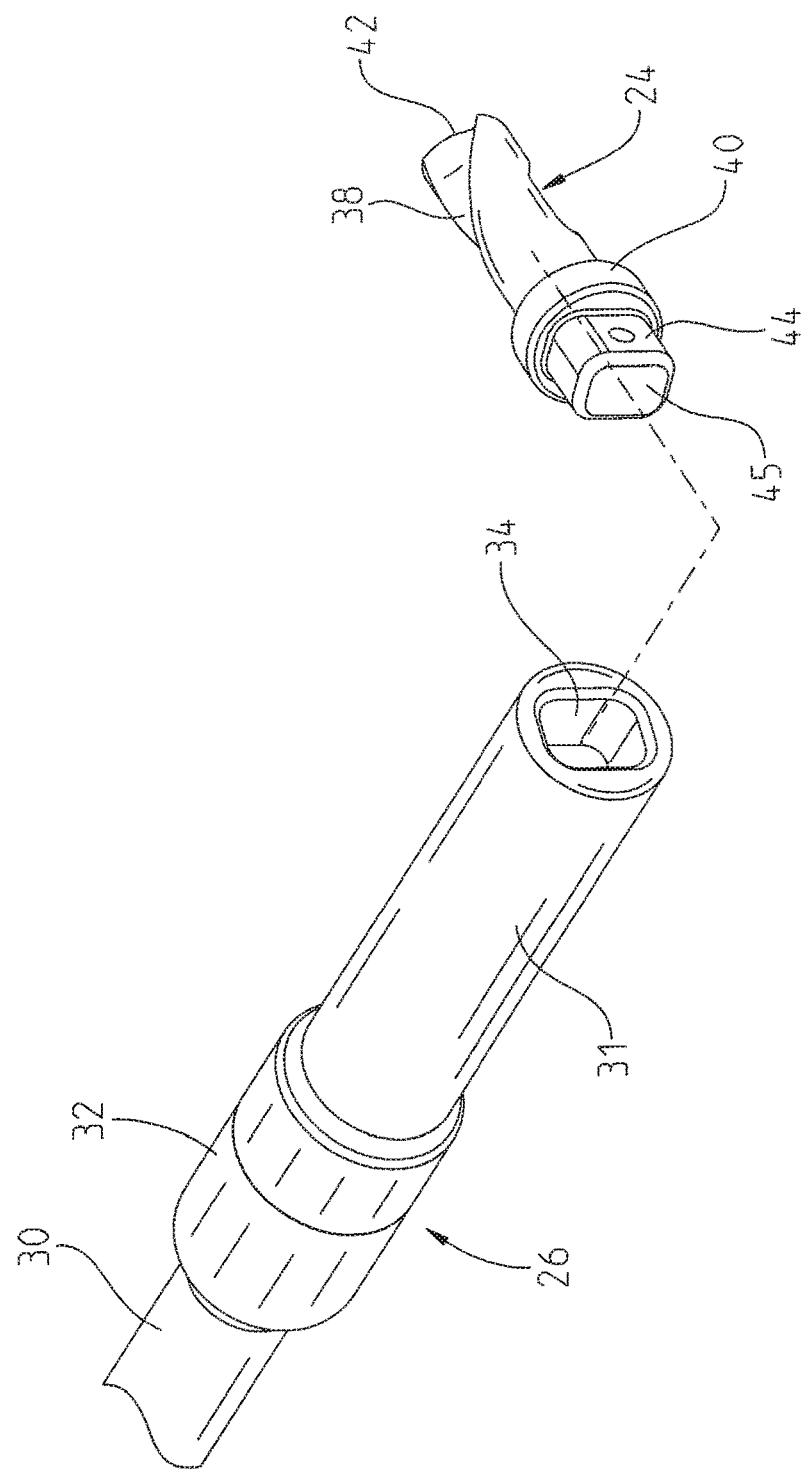
FIG. 3 represents a perspective exploded view of a portion of the illustrative quick-connect anti-rotation peg/drill bit assembly of FIG. 1.
Figure 4:
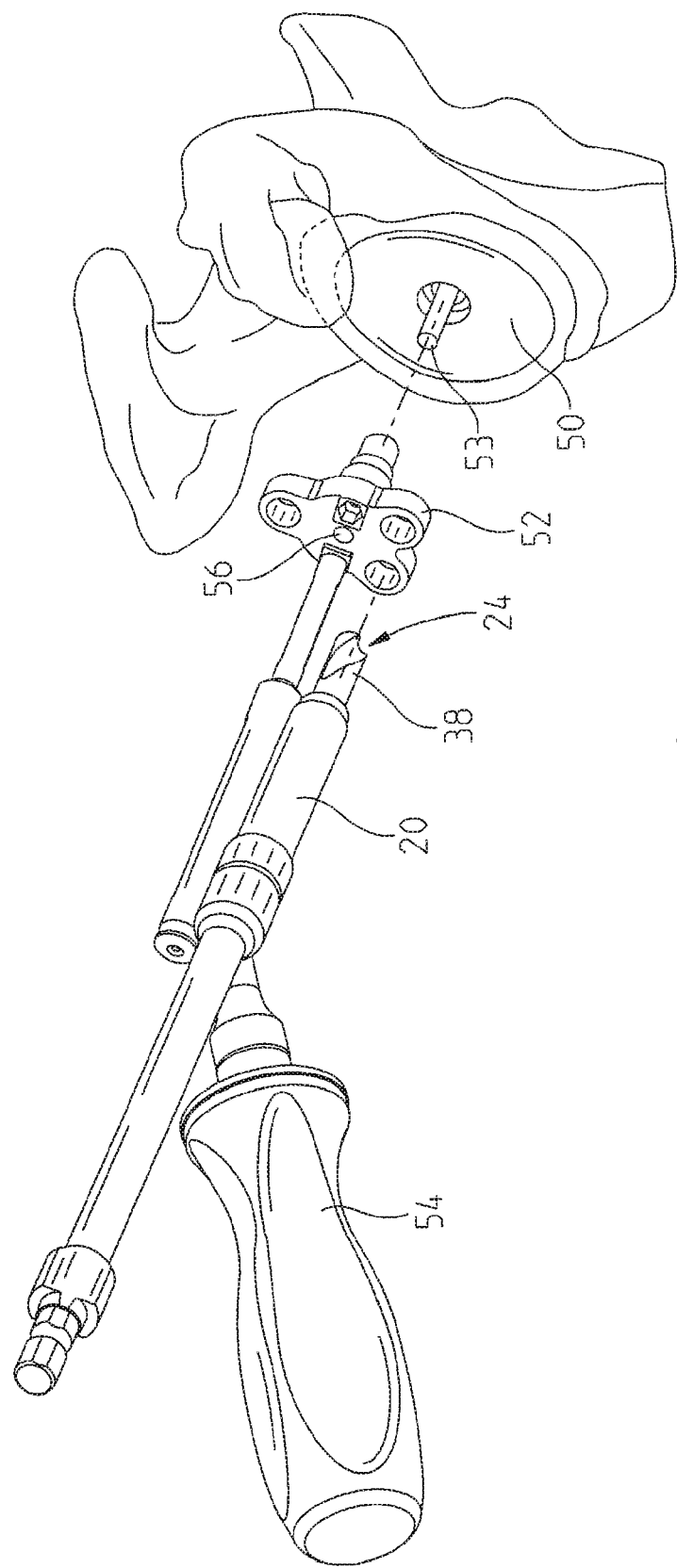
FIGS. 4-7 represent perspective views of a peripheral peg hole drilling procedure in which a quick-connect anti-rotation peg/drill bit component is left inserted within the glenoid cavity to serve as an anti-rotation peg in accordance with the teachings of the present application.

As shown in FIG. 2, in accordance with certain aspects of the present application, the second section 31 of the drive shank has an opening 34 opposite the collar portion 32, which is adapted to receive the drill bit 24 of the assembly 20. To create peripheral peg holes in the glenoid cavity when rotated by a drill, the drill bit 24 has a fluted portion 38 transitioning between a collar 40 and a cutting edge 42. The collar 40 of the drill bit 24 includes a stop surface 46 that is designed to provide a means for generating tactile feedback to the surgeon when the stop surface encounters the surface of the glenoid cavity, thereby indicating that the continued penetration of the drill bit 24 into the glenoid cavity should be ceased. In terms of the fluted portion 38, it should be understood and appreciated herein that the size, orientation and number of flutes comprising the fluted portion 38 of the drill bit 24 can be adjusted as necessary, particularly depending on the intended application and use of the drill bit assembly 20.

Adjacent the collar 40 of the drill bit 24, and opposite the cutting edge 42 of the fluted portion 38, is an attachment post 44 that is designed to correspondingly mate with the opening 34 and achieve a releasable connection between the second section 31 of the drive shank 26 and the drill bit 24. While this attachment can be achieved through any mechanical means known within the art (e.g., a press-fit engagement, a conventional Hudson connection, a square-drive quick-connection, a conventional drill chuck mechanism, a set screw, a tool clamp, a rivet, a snap ring, or the like), in accordance with certain aspects of the present application, a magnetic attachment is utilized to attach these components. In accordance with one specific embodiment in which a magnetic attachment is utilized, the drive shank 26 can be shaped such that it is able to accommodate a magnet (not shown) housed therein. In accordance with yet other specific embodiments in which a magnetic attachment is utilized, the bottom surface 45 of the attachment post 44 can be constructed of a material that produces a magnetic field (i.e., a force that pulls on other ferromagnetic materials, such as iron, nickel, cobalt and other such like alloys or metals) between the post 44 and the opening 34 of the second section 31 of the drive shank 26. In accordance with still other specific embodiments, the opening 34 of the drive shank's second section 31 may alternatively (or additionally) be made of or lined with a material that produces a magnetic field. As such, the present application is not intended to be limited in terms of how the magnetic connection is achieved.

Figure 5:
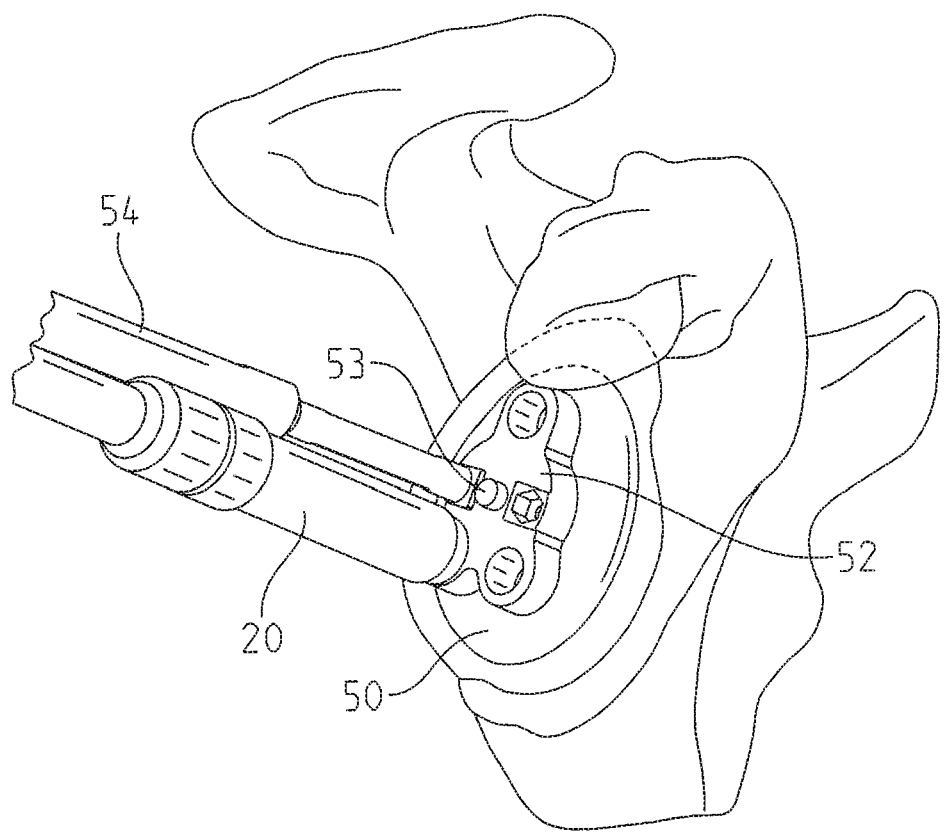

As mentioned above, unlike conventional glenoid processes, the present teachings eliminate the need to have separate anti-rotation pegs inserted into the bone after each peripheral peg hole is drilled. To accomplish this, the drill bits 24 used to create the peripheral peg holes also function as the anti-rotation pegs. An illustrative procedure demonstrating this unique aspect of the present application is now shown within FIGS. 4-7. Once the glenoid cavity 50 has been reamed to the proper version and inclination as determined by the preoperative plan and intraoperative observation, an appropriately sized peripheral peg drill guide 52 is attached to a quick-connect guide handle 54. The central hole 56 of the peripheral peg drill guide 52 is then advanced over a guide or alignment pin 53 (e.g., Steinman pin) that has been placed into glenoid cavity 50 as part of the glenoid preparation process. Once the peripheral peg drill guide 52 is fully seated against the face of the glenoid cavity 50 (FIG. 5), the quick-connect anti-rotation peg/drill bit assembly 20 is used to drill the first (superior) peripheral peg hole into the glenoid cavity 50 by advancing the fluted portion 38 of the drill bit 24 into the bone. Once the stop surface 46 of the drill bit's collar 40 engages the glenoid cavity 50, the drive shank 26 can be disconnected from the drill bit 24 (which is still left inserted into the glenoid cavity 50 through the drill guide 52). While not necessarily required herein, in accordance with certain aspects of the present application, it is recommended that the user wait until the drill bit 24 stops rotating before disconnecting it from the drive shank 26. Moreover, and as mentioned above, any known attachment means may be employed for releasably disconnecting the drive shank 26 from the drill bit 24 in accordance with the teachings of the present application. In accordance with specific embodiments, however, a magnetic attachment means may be used to releasably disassociate the drive shank 26 from the drill bit 24. According to this embodiment, friction created at the interface between the fluted portion 38 of the drill bit 24 and the glenoid bone contributes to the disruption of the magnetic connection between the two components such that the drill bit 24 is able to remain inserted within the glenoid cavity 50 as the drive shank 26 is removed from the joint.

Figure 6:
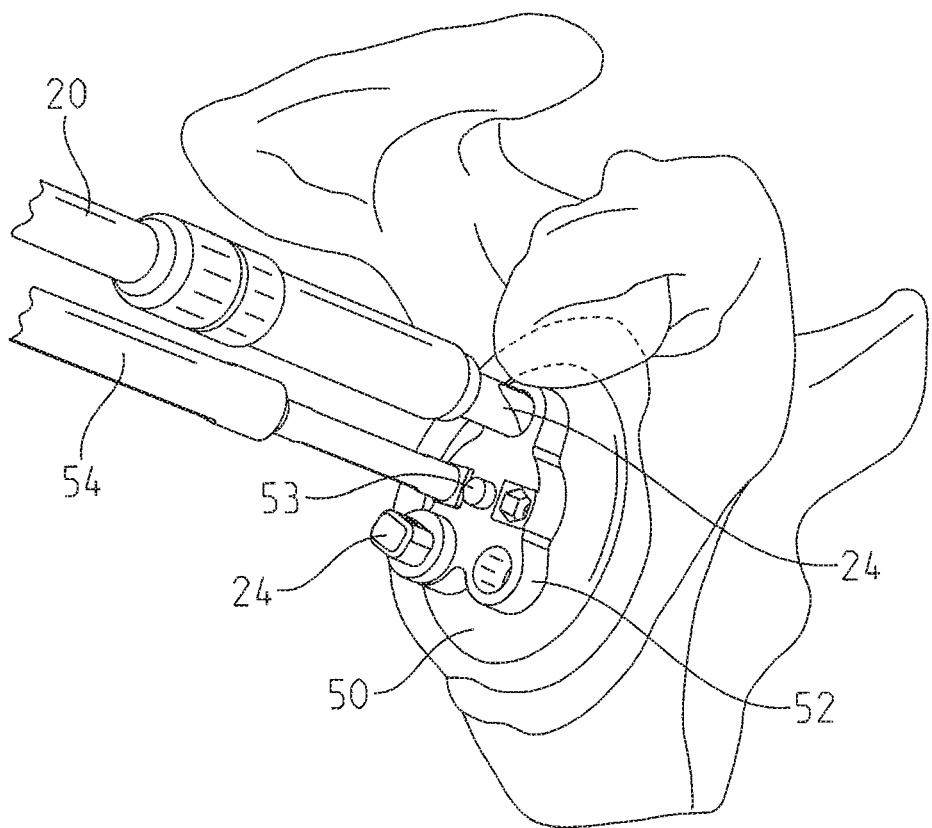
Figure 7:
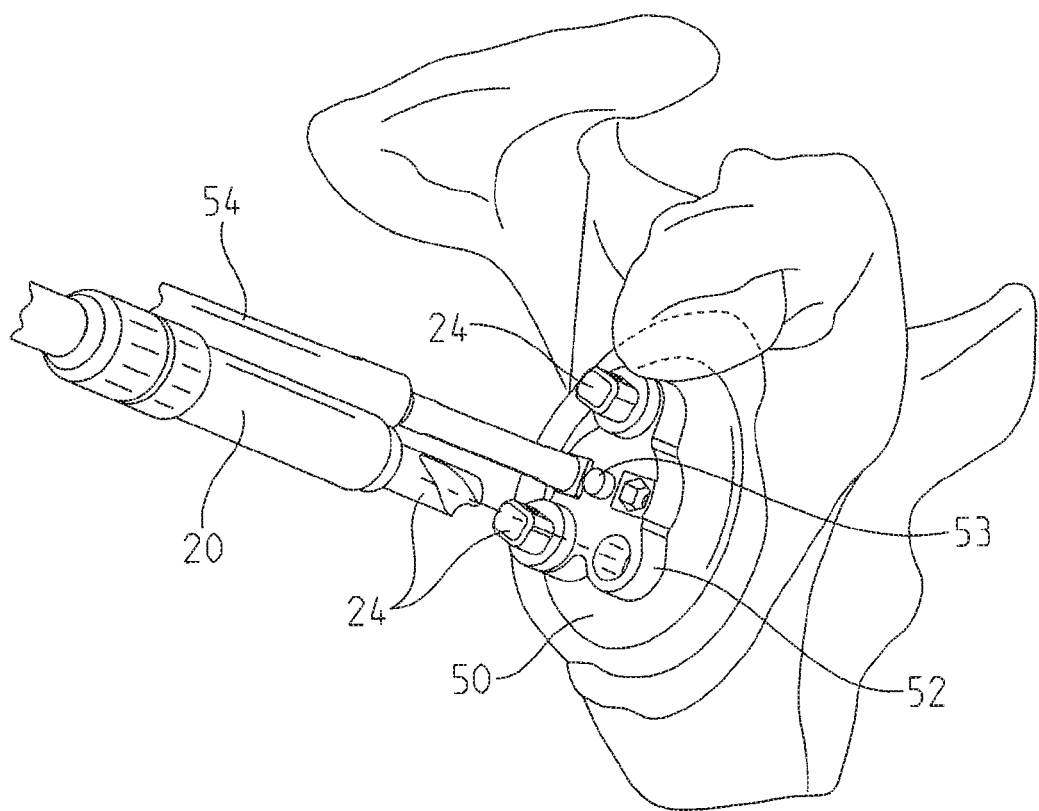

Second and third quick-connect anti-rotation peg/drill bit assemblies 20 are then used to create the respective second and third peripheral peg holes 58 within the glenoid cavity 50 (see FIGS. 6 and 7, respectively). The peripheral peg drill guide 52 is then removed from the joint by backing the guide over the alignment pin 53. The action of removing the peripheral peg drill guide 52 also causes the anti-rotation peg/drill bit assemblies 20 to disengage from the glenoid cavity 50. The alignment pin 53 is then removed from the glenoid cavity 50 by using the drill in reverse.

Figure 8:
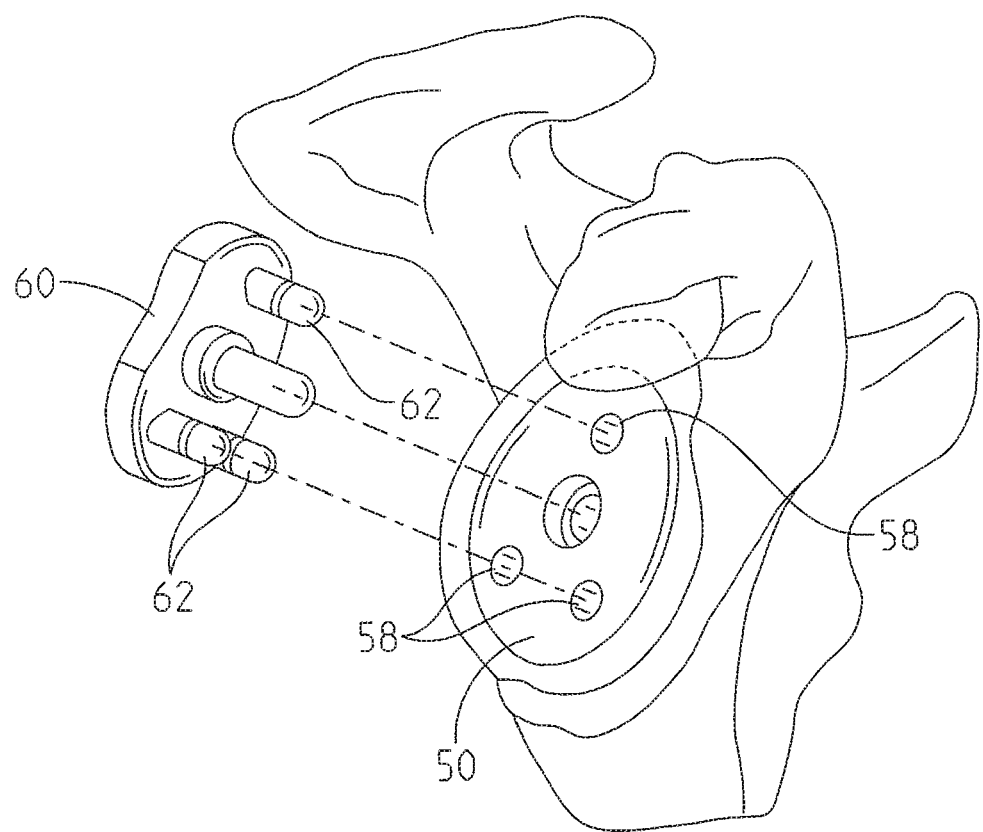
FIG. 8 represents a perspective view of a glenoid pegged component aligned for insertion into the peripheral peg holes drilled into the glenoid in accordance with the teachings of the present application.

As shown in FIG. 8, after the peripheral peg holes 58 are created, a glenoid component 60 can be implanted into the resected glenoid cavity 50 by aligning the peripheral pegs 62 of the glenoid component 60 with the drilled peripheral peg holes 58. It should be understood and appreciated herein that the teachings of the present application can be performed using various different geometrical peg configurations and shapes. For instance, while the present application depicts an illustrative embodiment in which the glenoid component 60 has three peripheral pegs 62, it is of course possible to perform the teachings of the present application using less or more than three peripheral pegs if desired. While not shown here, it is also envisioned that bone cement and/or various appropriate biological materials can be injected into the peripheral peg holes 58 defined within the glenoid cavity 50 before the peripheral pegs 62 of the glenoid component 60 are implanted to facilitate bonding of the component to the bone if desired. Those of skill in the art will understand how to incorporate such materials into the implantation system if necessary; therefore, a detailed discussion of the bonding process is not discussed in detail herein.

The material from which the anti-rotation peg/drill bit assemblies are made depends on the intended application of the assembly. For orthopedic uses, however, the drill bits can be manufactured from any surgical quality metallic component including, but not limited to, stainless steel, titanium, aluminum, brass, cobalt chrome molybdenum alloys, nitinol alloys and the like. It should also be understood and appreciated herein that the size, orientation and number of drill bits (and/or their respective flutes) can be adjusted as necessary, particularly depending on the intended application and use of the drill bits.

While an exemplary embodiment incorporating the principles of the present application has been disclosed hereinabove, the present application is not limited to the disclosed embodiments. Instead, this application is intended to cover any variations, uses, or adaptations of the application using its general principles. Further, this application is intended to cover such departures from the present disclosure as come within known or customary practice in the art to which this present application pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

What is claimed is:

1. A system for drilling into a glenoid bone, the system comprising:
   an alignment pin having a longitudinal axis and configured for insertion within the glenoid bone;
   a drill guide configured to advance over the longitudinal axis of the alignment pin extending from the glenoid bone, the drill guide defining first and second holes that extend through the drill guide parallel to the longitudinal axis;
   a drive shank configured to controllably impart rotation, the drive shank including a quick release mechanism;
   a first drill bit sized to match the first hole and configured to:
      rotate in response to rotation from the drive shank when the first drill bit is positioned in the first hole,
      detach from the drive shank via the quick release mechanism, leaving the first drill bit in the glenoid bone and in the first hole, and
      inhibit rotation of the drill guide with respect to the glenoid bone about the longitudinal axis; and
   a second drill bit sized to match the second hole and configured to:
      attach to the drive shank via the quick release mechanism, and
      rotate in response to rotation from the drive shank when the second drill bit is positioned in the second hole.

2. The system of claim 1, wherein the second drill bit is further configured to detach from the drive shank via the quick release mechanism, leaving the second drill bit in the glenoid bone and in the second hole.

3. The system of claim 1, wherein the second drill bit is further configured to inhibit rotation of the drill guide with respect to the glenoid bone about the longitudinal axis when the second drill bit is in the glenoid bone and in the second hole.

4. The system of claim 1, wherein the first drill bit includes a first collar sized larger than the first hole, the first collar configured to limit a depth drilled by the first drill bit.

5. The system of claim 1, wherein the second drill bit includes a second collar sized larger than the second hole, the second collar configured to limit a depth drilled by the second drill bit.

6. The system of claim 1, wherein the drill guide further defines a third hole that extends through the drill guide parallel to the longitudinal axis.

7. The system of claim 6, further comprising a third drill bit sized to match the third hole and configured to:
   attach to the drive shank via the quick release mechanism, and
   rotate in response to rotation from the drive shank when the third drill bit is positioned in the third hole.

8. The system of claim 7, wherein the third drill bit is further configured to detach from the drive shank via the quick release mechanism, leaving the third drill bit in the glenoid bone and in the third hole.

9. The system of claim 7, wherein the third drill bit includes a third collar sized larger than the third hole, the third collar configured to limit a depth drilled by the third drill bit.

10. The system of claim 1, further comprising a quick-connect guide handle connected to the drill guide and configured to advance an opening of the drill guide along the alignment pin until the drill guide is fully seated against the glenoid bone.

11. A system for drilling into a glenoid bone, the system comprising:
   an alignment pin configured for insertion within the glenoid bone;
   a drill guide configured to advance over the alignment pin along a longitudinal axis, the drill guide defining first, second, and third holes that extend through the drill guide parallel to the longitudinal axis;
   a drive shank configured to controllably impart rotation, the drive shank including a quick release mechanism;
   a first drill bit sized to match the first hole and configured to:
      rotate in response to rotation from the drive shank when the first drill bit is positioned in the first hole,
      detach from the drive shank via the quick release mechanism, leaving the first drill bit in the glenoid bone and in the first hole, and
      inhibit rotation of the drill guide with respect to the glenoid bone about the longitudinal axis when the first drill bit is in the glenoid bone and in the first hole;
   a second drill bit sized to match the second hole and configured to:
      attach to the drive shank via the quick release mechanism, and
      rotate in response to rotation from the drive shank when the second drill bit is positioned in the second hole,
      detach from the drive shank via the quick release mechanism, leaving the second drill bit in the glenoid bone and in the second hole, and
      inhibit rotation of the drill guide with respect to the glenoid bone about the longitudinal axis when the second drill bit is in the glenoid bone and in the second hole; and
   a third drill bit sized to match the third hole and configured to:
      attach to the drive shank via the quick release mechanism, and
      rotate in response to rotation from the drive shank when the third drill bit is positioned in the third hole.

12. The system of claim 11, wherein the third drill bit is further configured to detach from the drive shank via the quick release mechanism, leaving the third drill bit in the glenoid bone and in the third hole.

13. The system of claim 11, wherein the first drill bit includes a first collar sized larger than the first hole, the first collar configured to limit a depth drilled by the first drill bit.

14. The system of claim 11, wherein the second drill bit includes a second collar sized larger than the second hole, the second collar configured to limit a depth drilled by the second drill bit.

15. The system of claim 11, wherein the third drill bit includes a third collar sized larger than the third hole, the third collar configured to limit a depth drilled by the third drill bit.

16. The system of claim 11, further comprising a quick-connect guide handle connected to the drill guide and configured to advance an opening of the drill guide along the alignment pin until the drill guide is fully seated against the glenoid bone.

17. A system for drilling into a glenoid bone, the system comprising:
an alignment pin configured for insertion within the glenoid bone;
a drill guide configured to advance over the alignment pin along a longitudinal axis, the drill guide defining first, second, and third holes that extend through the drill guide parallel to the longitudinal axis;
a drive shank configured to controllably impart rotation, the drive shank including a quick release mechanism;
a first drill bit sized to match the first hole and configured to:
rotate in response to rotation from the drive shank when the first drill bit is positioned in the first hole,
detach from the drive shank via the quick release mechanism, leaving the first drill bit in the glenoid bone and in the first hole, and
inhibit rotation of the drill guide with respect to the glenoid bone about the longitudinal axis when the first drill bit is in the glenoid bone and in the first hole,
the first drill bit including a first collar sized larger than the first hole, the first collar configured to limit a depth drilled by the first drill bit;
a second drill bit sized to match the second hole and configured to:
attach to the drive shank via the quick release mechanism, and
rotate in response to rotation from the drive shank when the second drill bit is positioned in the second hole,
detach from the drive shank via the quick release mechanism, leaving the second drill bit in the glenoid bone and in the second hole, and
inhibit rotation of the drill guide with respect to the glenoid bone about the longitudinal axis when the second drill bit is in the glenoid bone and in the second hole,
the second drill bit including a second collar sized larger than the second hole, the second collar configured to limit a depth drilled by the second drill bit; and
a third drill bit sized to match the third hole and configured to:
attach to the drive shank via the quick release mechanism, and
rotate in response to rotation from the drive shank when the third drill bit is positioned in the third hole;
the third drill bit including a third collar sized larger than the third hole, the third collar configured to limit a depth drilled by the third drill bit.

18. The system of claim 17, wherein the third drill bit is further configured to detach from the drive shank via the quick release mechanism, leaving the third drill bit in the glenoid bone and in the third hole.

19. The system of claim 17, further comprising a quick-connect guide handle connected to the drill guide and configured to advance an opening of the drill guide along the alignment pin until the drill guide is fully seated against the glenoid bone.

* * * * *